(12) United States Patent
Christakos

(10) Patent No.: US 7,033,996 B2
(45) Date of Patent: Apr. 25, 2006

(54) METHOD FOR THE TREATMENT OF VITAMIN D RELATED DISEASE

(75) Inventor: Sylvia Christakos, Mendham, NJ (US)

(73) Assignee: University of Medicine & Dentistry of New Jersey, New Brunswick, NJ (US)

( * ) Notice: Subject to any disclaimer, the term of this patent is extended or adjusted under 35 U.S.C. 154(b) by 265 days.

(21) Appl. No.: 10/232,342

(22) Filed: Aug. 30, 2002

(65) Prior Publication Data

US 2004/0214257 A1    Oct. 28, 2004

Related U.S. Application Data

(60) Provisional application No. 60/316,941, filed on Aug. 31, 2001.

(51) Int. Cl.
*A61K 38/00*    (2006.01)
*C07K 14/00*    (2006.01)

(52) U.S. Cl. .......................................... 514/2; 530/350
(58) Field of Classification Search ................ 530/350; 514/2

See application file for complete search history.

(56) References Cited

U.S. PATENT DOCUMENTS

2003/0166586 A1 * 9/2003 Sealy ........................... 514/44

OTHER PUBLICATIONS

Baran et al., "Rapid actions of 1α, 25-dihydroxyvitamin $D_3$ on $Ca^{2+}$ and phospholipids in isolated rat liver nuclei", Feb. 1989 259(1) :205-208.
Chen et al., "Cloning of the human 1α, 25-dihydroxyvitamin D-3 24-hydroxylase gene promoter and identification of two vitamin D-responsive elements", Biochimica et Biphysica Acta 1995 1263 : 1-9.
Civitelli et al., "Nongenomic Activation of the Calcium Message System by Vitamin D Metabolites in Osteoblast-like Cells", Endocrinology 1990 127 (5) :2253-2262.
Feldman et al., "Rapid Biological Responses Mediated by 1α, 25-Dihydroxyvitamin $D_3$:A Case Study of Transcaltachia (Rapid Hormonal Stimulation of Intestinal Calcium Transport)", 1997 Chapter 15 233-256.
Kerry et al., "Transcriptional Synergism between Vitamin D-responsive Elements in the Rat 25-Hydroxyvitamin $D_3$ 24-Hydroxylase (*CYP24*) Promoter", J. Biol. Chem. 1996 271 (47) :29715-29721.
Lieberherr et al., "A Functional Cell Surface Type Receptor Is Required for the Early Action of 1,25-Dihydroxyvitamin $D_3$ on the Phosphoinositide Metabolism in Rat Enterocytes", J. Biol. Chem/ 1989 264 (34) :20403-20406.
Lowe et al., "Vitamin D-Mediated Gene Expression", Critical Reviews in Eukaryotic Gene Expression 1992 2 (1) :65-109.
Minghetti et al., "1, 25 (OH) $_2$ receptors: gene regulation and genetic circuitry", FASEB 1988 2 (15) : 3043-3053.
Nemere et al., "Identification of a Specific Binding Protein for 1α, 25-Dihydroxyvitamin $D_3$ in Basal-Lateral Membranes of Chick Intestinal Epithelium and Relationship to Transcaltachia", J. Biol. Chem. 1994 269 (38) :23750-23756.
Nemere et al., "Calcium Transport in Perfused Doudena from Normal Chicks:Enhancement within Fourteen Minutes of Exposure to 1, 25- Dihydroxyvitamin $D_3$ ", Endocrinology 1984 115 (4) : 1476-1483.
Norman et al., "The Vitamin D Endocrine System:Steroid Metabolism, Hormone Receptors, and Biological Response (Calcium Binding Proteins)", Endocrine Reviews 1982 3 (4) :331-366.
Ohyama et al., "Identification of a Vitamin D-responsive Element in the 5'-Flanking Region of the Rat 25-Hydroxyvitamin $D_3$ 24-Hydroxylase Gene", J. Biol. Chem. 1994 269 (140:10545-10550.
Pike, J. Wesley, "Vitamin $D_3$ Receptors : Structure and Function in Transcription", Annu. Rev. Nutr. 1991 11: 189-216.
Tsutsumi et al., "Effect of 1, 25-dihydroxyvitamin $D_3$ on phospholipid composition of rat renal brush border membrane", Am. J. Physiol. 1985 294:F117-F123.
Zierold et al., "Identification of a vitamin D-response element in the rat calcidiol (25-hydroxyvitamin $D_3$) 24-hydroxylase gene", Proc. Natl. Acad. Sci. USA 1994 91: 900-902.

* cited by examiner

*Primary Examiner*—James Ketter
*Assistant Examiner*—Tara L Garvey
(74) *Attorney, Agent, or Firm*—Licata & Tyrrell P.C.

(57) ABSTRACT

The present invention provides a method for treating diseases caused by either an excess or diminution of Vitamin $D_3$. It provides pharmaceutical compositions for the treatment of such diseases and the methods by which these compositions are to be used. Also provided are methods for testing the activity of both 24(OH)ase and CCAATT/Enhancer Binding Protein β (C/EBPβ), as well as, for testing the effect of a compound on 24(OH)ase and C/EBPB activity activity. In particular embodiments, a method is provided for reducing the risk of hypercalcemia when administering 1,25(OH)$_2$D$_3$ or its analogs for the treatment of vitamin D diseases. Methods for both enhancing and diminishing 24(OH)ase activity are also provided.

5 Claims, 2 Drawing Sheets

Figure 1A-E
1A. UMR osteoblastic cells
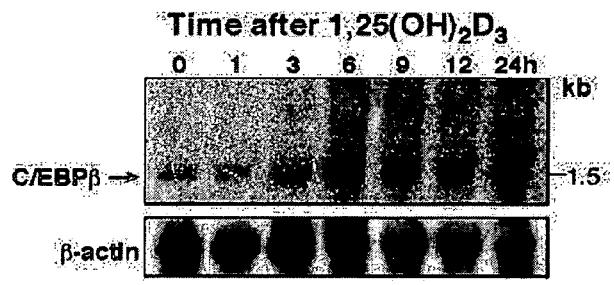
1B. Primary osteoblasts
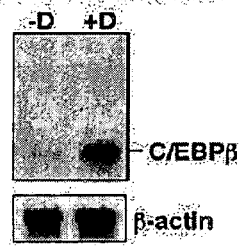
1C. mouse kidney
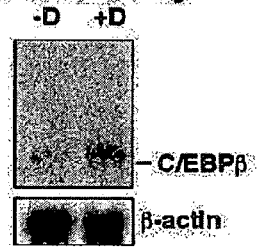
1D. 24(OH)ase (-1367/+74)
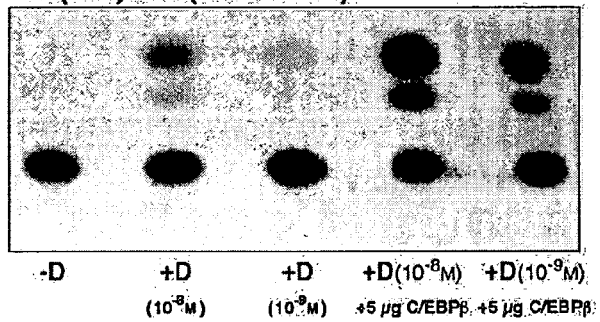
1E. Western Blot
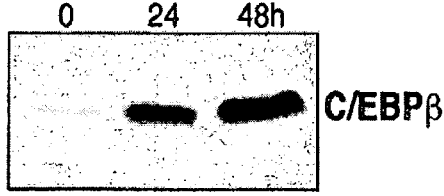

hVDR (1500/+60)luc

METHOD FOR THE TREATMENT OF VITAMIN D RELATED DISEASE

CROSS-REFERENCE TO RELATED APPLICATION

This application claims priority to provisional application No. 60/316,941 filed Aug. 31, 2001 the disclosure of which is incorporated herein by reference.

GOVERNMENT INTEREST

This invention was made with government support. The government may have certain rights in the present invention.

FIELD OF THE INVENTION

The present invention provides a method for treating diseases caused by either an excess or diminution of Vitamin $D_3$. In another embodiment, it provides a method for testing the activity of both 24-hydroxylase [24(OH)ase] and C/EBPβ as well as for testing the effect of a compound on said activity. In a further embodiment, a method is provided for the selective induction of CCAATT/Enhancer Binding Protein β (C/EBPβ).

DESCRIPTION OF THE PRIOR ART

Vitamin D is a prohormone of several active metabolites that behave as hormones. Serious diseased states have been associated with the deficiency of vitamin D, such as rickets in children and osteomalacia in adults. The most biologically reactive metabolite of vitamin D is $1,25(OH)_2D_3$.

Vitamin $D_3$ is a secosteroid responsible for a diverse array of biological responses that include maintenance of calcium homeostasis, immunomodulation and selected cell differentiation. It is formed in human skin by exposure to ultraviolet radiation. In the skin, previtamin $D_3$ is synthesized photochemically from 7-dehydrocholesterol and is slowly isomerized to vitamin $D_3$. Vitamin $D_3$ enters the circulation and binds to vitamin D binding protein (DBP) for transport. DBP-bound vitamin $D_3$ is biologically inert. It is converted in the liver, at the C-25 position by a cytochrome P-450 enzyme, into 25-hydroxyvitamin $D_3$ (monohydroxyvitamin $D_3$), the major circulating form of vitamin $D_3$. In the kidney and in other tissues, 25-hydroxyvitamin $D_3$ is further hydroxylated to a more metabolically active form known as 1,25-dihydroxyvitamin $D_3$ [$1,25(OH)_2D_3$] which functions to increase calcium absorption from the intestine and promote normal bone formation and mineralization. Hence, Vitamin D is an important substance required for calcium homeostasis in the human body.

The biologically active metabolite $1,25(OH)_2D_3$ interacts with the cell to evoke various biological responses in at least two distinct ways. One way that $1,25(OH)_2D_3$ may interact with the cell is via a nuclear receptor for the regulation of gene transcription. ((*Crit. Rev. Eukar. Gene Exp.*, 2:65–109 (1992), *Annual Rev. Nutr.*, 11:189–216 (1991), *Vitamin D: Gene Regulation, Structure-Function Analysis and Clinical Application*, Norman, A. W, Bouillon, R., and Thomasset, M., Eds., pp. 146–154, Walter de Gruyter, Berlin, Germany (1991)). The nuclear receptor for $1,25(OH)_2D_3$ is the Vitamin $D_3$ Receptor (VDR). It is a member of family II of the hormone receptor superfamily of transcription factors. VDR has been fully characterized and is primarily localized in the nuclear compartment of the cell.

In the cell nucleus, VDR, in the presence of $1,25(OH)_2D_3$, heterodimerizes with the retinoid X receptor (RXR). This dimeric complex binds to a vitamin D responsive element (VDRE, characterized by direct repeats of the hexamer AGGTCA spaced by three nucleotides) and activates vitamin D responsive genes. $1,25(OH)_2D_3$ binds to its intracellular receptor, the VDR, with high affinity and specificity resulting in transcriptional activation of vitamin D target genes such as those for the bone proteins osteocalcin and osteopontin. The nuclear receptor for $1,25(OH)_2D_3$ has been shown to be present in 30 different tissues and it belongs to the same super family of proteins that includes receptors for the steroid hormones, retinoic acid and thyroxin (*Crit. Rev. Eukar. Gene Exp.*, 2:65–109 (1992), *FASEB J.*, 2:3043–3053 (1988), *Endocr. Rev.*, 3:331–366 (1982)).

The $1,25(OH)_2D_3$-VDR complex also regulates a key metabolic enzyme, 25-hydroxyvitamin $D_3$-24-hydroxylase [24(OH)ase]. Activation of this enzyme occurs through receptor binding to discrete regulatory regions within the promoter of this gene. Once activated, transcription levels of 24(OH)ase increase and a greater quantity of the protein is produced. The 24(OH)ase protein then functions, in a negative feed back loop, to metabolize $1,25(OH)_2D_3$ to the biologically inert trihydroxy vitamin $D_3$ [$1,24,25(OH)_3 D_3$] by hydroxylating C24. This inert intermediate is later metabolized to calcitroic acid.

In addition to the cell nuclear response evoked by $1,25(OH)_2D_3$, it has been recently discovered that $1,25(OH)_2D_3$ also mediates biological responses by a rapid non-nuclear mechanism (*Vitamin D: Gene Regulation, Structure-Function Analysis and Clinical Application*, Norman, A. W., Bouillon, R., and Thomasset, M., Eds., pp. 146–154, Walter de Gruyter, Berlin, Germany (1991); and *Endocrinology*, 115:1476–1483 (1984)). Recent discoveries have identified a series of rapid cell-surface signaling effects of $1,25(OH)_2D_3$ that occur within seconds to minutes of exposure of cells to this steroid hormone (*Rapid biological responses mediated by $1,25(OH)_2D_3$: A case study of transcaltachia*, pp. 233–256, in *Vitamin D*, Feldman D. M, Glorieux, F. H., Pike, J. W., Eds., Academic Press, San Diego, Calif., (1997)). Evidence supporting the existence of a membrane receptor for $1,25(OH)_2D_3$ that mediates the initiation of rapid responses in some cells is described in *J. Biol. Chem.*, 264:20403–20406 (1989); and *J. Biol. Chem.*, 269:23750–23756 (1994). An example of cell-surface $1,25(OH)_2D_3$ evoked responses include the opening of voltage-gated Ca.sup.2+ channels in rat osteosarcoma cells, as described in *Endocrinology*, 127:2253–2262 (1990) and *Am. J. Physiol.*, 249:F117–F123 (1985), as well as other rapid effects in kidney, as described in *FEBS Lett.*, 259:205–208 (1989).

The $1,25(OH)_2D_3$ metabolite functions to enhance intestinal absorption of dietary calcium and it plays a key role in the mobilization of calcium stores from bone. A disruption in calcium homeostasis can lead to many diseased states including rickets, osteomalacia, osteoporosis, osteopenia, osteosclerosis, renal osteodystrophy; skin diseases, such as psoriasis; thyroid diseases, such as medullary carcinoma; brain diseases, such as Alzheimer's disease; parathyroid diseases, such as hyperparathyroidism, hypoparathyroidism, pseudoparathyroidism or secondary parathyroidism; liver and pancreas diseases, such as diabetes, cirrhosis, obstructive jaundice or drug-induced metabolism; intestine diseases, such as glucocorticoid antagonism, idiopathic hypercalcemia, malabsorption syndrome, steatorrhea, or tropical sprue; kidney disease, such as chronical renal disease, hypophosphatemic vitamin D-resistant rickets or vitamin D-dependent rickets; and lung diseases, such as sarcoidosis.

The treatment of these diseased states requires a fundamental balancing of Calcium homeostasis that, if not monitored appropriately, can lead to hypercalcemia, that may cause soft tissue calcification which can also lead to death. There is therefore a need to both reduce and/or prevent the risk of hypercalcemia, which is a potential threat in the treatment of vitamin D3 deficiency associated diseases, and to treat those who suffer from high calcium serum levels.

SUMMARY OF THE INVENTION

The present invention provides a method for treating diseases caused by either an excess or diminution of Vitamin $D_3$. In another embodiment, it provides a method for testing the activity of both 24(OH)ase and CCAATT/Enhancer Binding Protein β (C/EBPβ) as well as for testing the effect of a compound on said activity. In a further embodiment, a method is provided for the selective induction of C/EBPβ. In particular embodiments, is provided a method for reducing the risk of hypercalcimia when administering $1,25(OH)_2D_3$ or its analogs for the treatment of vitamin D diseases.

The present invention is primarily based on the discovery that the 24-hydroxylase gene contains two putative binding sites (one proximal and one distal) for C/EBPβ and that C/EBPβ binding to these sites increases the transcription rate of 24(OH)ase by binding to these sites (i.e., the proximal binding site is the important site for the enhancement of transcription), and therefore it enhances $1,25(OH)_2D_3$ induction of 24(OH)ase transcription. Further, C/EBPβ mRNA is upregulated in the presence of $1,25(OH)_2D_3$, which is indicative of the activation of 24(OH)ase transcription. mRNA induction and 24(OH)ase production are sensitive markers of vitamin D activity in vivo. Hence, both C/EBPβ and 24(OH)ase mRNA levels can be used to measure vitamin D activity. Thus, by controlling the cellular concentration of C/EBPβ the rate of 24-hydroxylase transcription can be increased or decreased thus affecting vitamin D activity in vivo. Additionally, it has been determined that C/EBPβ enhances vitamin D receptor transcription by activation of protein kinase A.

In particular, the current invention relates to the molecular action of 1,25 dihydroxyvitamin $D_3$ [$1,25(OH)_2D_3$], 24(OH) ase and C/EBPβ and concerns the therapeutic properties of C/EBPβ for the regulation of cellular responses affecting Vitamin $D_3$ concentration. More specifically, the present invention concerns pharmaceutical compositions comprising C/EBPβ for the enhancement of 24(OH)ase transcription and the maintenance of calcium homeostasis. A method for the reduction of 24(OH)ase transcription activity by the administration of a test compound found to block C/EBPβ activity is also provided.

The methods of the invention are useful for treatment of hypercalcemia, elevated serum calcium, that may cause soft tissue calcification, which can be life threatening. Other diseased states for which the methods of the invention may be used in conjunction with the administration of vitamin $D_3$ and/or its analogs include rickets, osteomalacia, osteoporosis, osteopenia, osteosclerosis, renal osteodystrophy; skin diseases, such as psoriasis; thyroid diseases, such as medullary carcinoma; brain diseases, such as Alzheimer's disease; parathyroid diseases, such as hyperparathyroidism, hypoparathyroidism, pseudoparathyroidism or secondary parathyroidism; liver and pancreas diseases, such as diabetes, cirrhosis, obstructive jaundice or drug-induced metabolism; intestine diseases, such as glucocorticoid antagonism, idiopathic hypercalcemia, malabsorption syndrome, steatorrhea, or tropical sprue; kidney disease, such as chronical renal disease, hypophosphatemic vitamin D-resistant rickets or vitamin D-dependent rickets; lung diseases, such as sarcoidosis; and for treatment of any other disease in which vitamin $D_3$ or its pro-drugs are involved.

In a first embodiment the invention is a pharmaceutical composition that includes an effective amount of a C/EBPβ protein, or the nucleotide sequence coding for the protein, or a fragment coding for the active region of the protein, for the treatment of diseases associated with excess $1,25(OH)_2D_3$, such as hypercalcemia. Methods for the treatment of such diseases, using the C/EBPβ protein, or the nucleotide sequence coding for the protein, are also described.

In a further embodiment a method is described for reducing the risk of hypercalcemia when administering $1,25(OH)_2D_3$ or its analogs for the treatment of vitamin D deficient disease, which involves the administration of a composition containing the C/EBPβ protein, or the nucleotide sequence coding for the protein, along with the administration of $1,25(OH)_2D_3$ or its analogs.

In another embodiment is provided a method for testing both the activity of C/EBPβ and 24(OH)ase for determining whether a possible compound exhibits inhibitory effects on $1,25(OH)_2D_3$ activity in a cell (e.g., LLCKL cells, kidney cells, COS monkey cells, UMR Osteoblastic cells or even skin) which method includes applying the test compound to a viable cell, determining the amount of C/EBPβ mRNA or C/EBPβ in the cell following the delivery of the test compound (e.g., by microinjection, etc.), and comparing the concentration determined (of mRNA or the C/EBPβ) to a control; an increase in the amount of C/EBPβ mRNA or C/EBPβ in the cell relative to the control indicates the compound has an inhibitory effect on the concentration of $1,25(OH)_2D_3$ in the cell, where as a decrease would mean that it has an enhancing effect.

In still another aspect, the invention provides a method for determining whether a candidate compound increases or inhibits C/EBPβ activity, which comprises inducing C/EBPβ activity in vivo in a cell (such as LLCKL Kidney Cells, COS monkey cells, UMR Osteoblastic or skin cells), biopsying cells in which the C/EBPβ was induced, dividing the biopsied cells into two groups, adding a tagged monohydroxyvitamin $D_3$ to a first group of cells and thereafter measuring the amount of tagged dihydroxyvitamin $D_3$, adding a tagged monohydroxyvitamin $D_3$ plus the candidate compound to a second group of cells and thereafter measuring the amount of tagged dihydroxyvitamin $D_3$, wherein a lesser amount of tagged dihydroxyvitamin $D_3$ in the second group tested indicates activation and a greater amount indicates inhibition of C/EBPβ activity or induction thereof.

In yet another embodiment, a pharmaceutical composition containing a mutated C/EBPβ protein is provided. As an example, the mutated C/EBPβ protein may contain a defective 24(OH)ase binding region, i.e., caused by a mutation(s) in the nucleotide sequence coding for the C/EBPβ protein between basepairs −395 to −388 and basepairs −964 to −955 of SEQ. ID. 1. These mutations can be generated by standard procedures well known to those skilled in the art, such as by causing a point mutation. (i.e., by U.V. light) or by gene rearrangement. The pharmaceutical composition includes an acceptable biological carrier, wherein an effective amount it is suitable for treatment of a disease associated with diminished calcium absorption, such as osteoporosis. A method for the treatment of a disease associated with diminished calcium absorption in a subject, comprising administering to the subject a pharmaceutical composition that comprises an effective amount of a mutated C/EBPβ protein, is also provided.

A pharmaceutical composition comprising an effective amount of a protein that inhibits C/EBPβ activity, with a biologically acceptable carrier, is also described, along with a method for the treatment of a disease associated with a vitamin D3 deficiency. This method includes administering to a subject a pharmaceutical composition that has an effective amount of a compound that inhibits C/EBPβ activity. A method for the selective induction of C/EBPβ involving the administration of a pharmaceutical composition that includes $1,25(OH)_2D_3$ or its analogs is also described.

BRIEF DESCRIPTION OF THE DRAWINGS

Referring particularly to the drawings for the purpose of illustration only and not limitation, there is illustrated:

FIG. 1 [A–E] is an illustration of C/EBPβ is induced by $1,25(OH)_2D_3$ [Northern blot analysis of mRNA from 1,25 $(OH)_2D_3$ treated UMR cells ($10^{-3}$M; A), primary murine osteoblasts ($10^{-3}$M, 9 h; B) and the kidney of $1,25(OH)_2D_3$ injected vitamin D deficient mice (C)] and enhances VDR mediated 24(OH)ase transcription [COS cells were cotransfected with hVDR and C/EBPβ and treated with $1,25(OH)_2D_3$ for 24 h] (D).

DESCRIPTION OF THE PREFERRED EMBODIMENT

Figure 2:
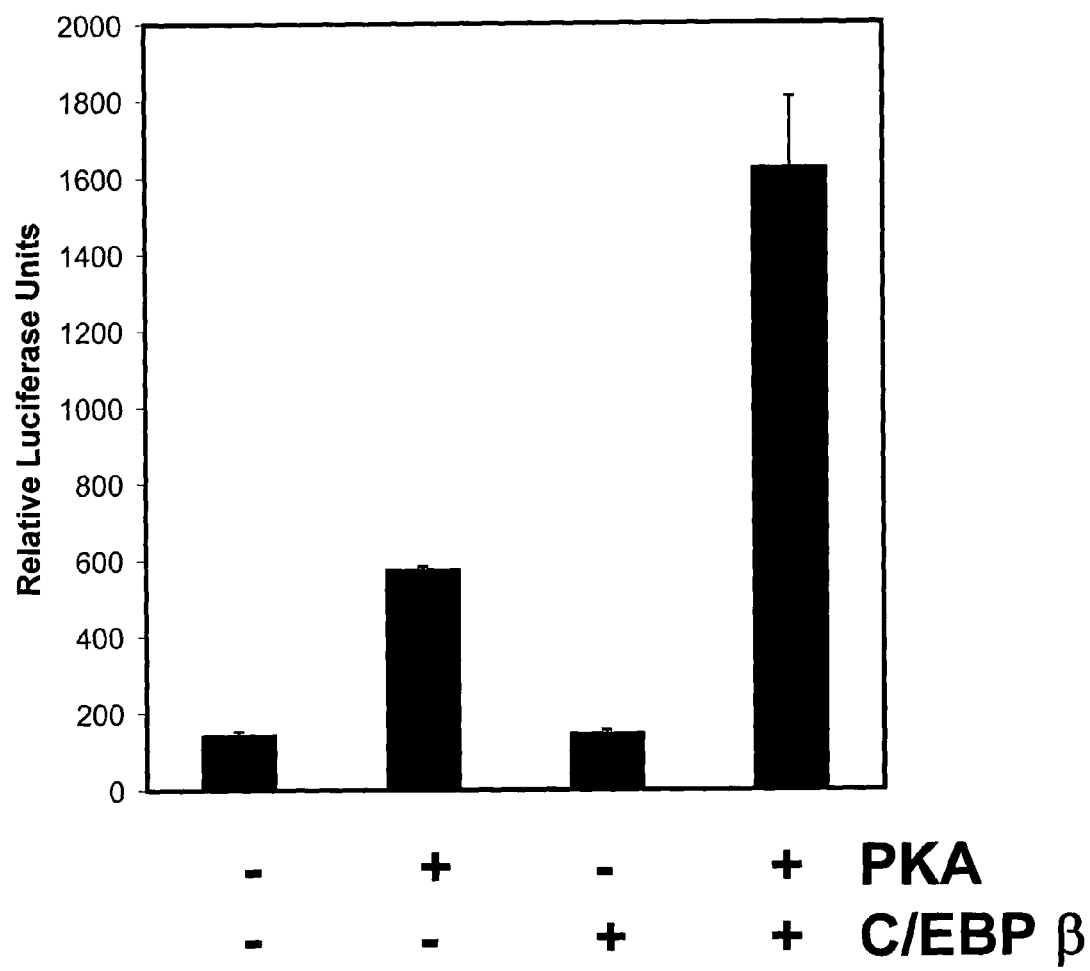
FIG. 2 is an illustration of C/EBPβ enhancement of PKA mediated transcriptional activation of hVDR. 2 μg of the VDR promoter (−1500/+60) cotransfected in JEG cells with 1 μg of PKA expression vector in the presence or absence of 5 μg C/EBPβ.

In the studies herein described, using gene chip arrays a gene heretofore unknown to be induced by $1,25(OH)_2D_3$, was found to be activated by $1,25(OH)_2D_3$ by a factor greater than 50% in kidney. The protein was isolated, verified by Northern Blot analysis of kidney as well as osteoblastic mRNAs, and found to be a CCAATT enhancer binding protein β (C/EBPβ). The C/EBPs are a family of transcription factors that regulate genes of the acute phase response as well as genes involved in cell growth, differentiation and cell type specific genes. Previous studies have indicated that C/EBP family members are expressed in kidney and osteoblasts and are involved in the regulation of IGF, prostaglandin G/Hsynthase 2 and osteocalcin expression in osteoblasts.

Through the herein described studies, the inventors have discovered two putative C/EBPβ binding sites in the 24(OH) ase promoter and have marked the enhancement of VDR mediated 24(OH)ase transcription in the presence of C/EBPβ. These sites are located at positions −395 to −388 and −964 to −955, in the promoter region of the 24(OH)ase gene. For a description of the 24(OH)ase gene and reporter region see: Ohyama, Y, Ozono, K et al *J. Biol. chem.* 269 10545–10550,1994 (*rat 24(OH)ase promoter*), Zierold, C, Darwish, H M and DeLuca, H. F. *Proc. Natl. Acad. Sci USA* 91: 900–902 (1994), Kerry, D. M., Dwivedi, P. P et al *J. Biol Chem* 271: 29715–29721 (1996) and for the Human 24(OH) ase promoter—Chen K. S. and DeLuca H. F. *Biochim. Biophys. Acta* 1263: 1–9 (1995) herein incorporated by reference.

Since C/EBPβ is induced by protein kinase A activation in different cell types including osteoblasts, it is indeed possible that the cross-talk of the PKA signaling pathway, and PTH with $1,25(OH)_2D_3$ may converge on changes in C/EBPβ expression. Thus, studies have been conducted to examine the mechanisms involved in the modulation of VDR mediated 24(OH)ase transcription by C/EBPβ as well as the role of C/EBPβ in the cross talk we have observed between the protein kinase A signaling pathway and PTH and $1,25(OH)_2D_3$ induced 24(OH)ase transcription.

These studies have established C/EBPβ as a novel 1,25 $(OH)_2D_3$ target gene and that it is a key factor in the regulation of 24(OH)ase as well as in the cross talk between PTH and $1,25(OH)_2D_3$ action. A greater understanding of this novel cofactor and target protein involved in $1,25(OH)_2D_3$ action will provide important new insight in our understanding of the mechanism of $1,25(OH)_2D_3$ action in the maintenance of calcium homeostasis. See Example 1, herein.

Relatively few $1,25(OH)_2D_3$ regulated genes are known in target tissues maintaining calcium homeostasis. Our results using Gene Chip array (which are the first to apply Gene Chip arrays to the study of $1,25(OH)_2D_3$ action (Peng et al. abstract ASBMR meeting, October 2001), confirmed that the gene expressed in highest concentrations in the kidney in response to $1,25(OH)_2D_3$ is 24(OH)ase (43 fold induction). Another gene besides 24(OH)ase activated by a factor greater than 50% by $1,25(OH)_2D_3$ and verified by Northern blot analysis was C/EBPβ (FIG. 2, A–C). There are two putative C/EBPβ sites, in the rat 24(OH)ase promoter and in our results we have observed markedly enhanced $1,25(OH)_2D_3$ induced 24(OH)ase transcription in the presence of C/EBPβ (FIG. 2D). Thus, by applying Gene Chip arrays to the study of $1,25(OH)_2D_3$ action, we identified a novel $1,25(OH)_2D_3$ target genes and have used this information to begin providing new insight into the mechanism of $1,25(OH)_2D_3$ transcriptional regulation in the kidney.

The identification of C/EBPβ by Gene Array as a transcription factor induced by $1,25(OH)_2D_3$, which we have found enhances 24(OH)ase transcription, has provided new insight into the molecular mechanisms involved in regulating $1,25(OH)_2D_3$ target gene expression and represents an extension of current understandings related to VDR mediated 24(OH)ase transcription.

C/EBPβ has been demonstrated in the kidney. Our results represent the first evidence of $1,25(OH)_2D_3$ upregulation of C/EBPβ in kidney as well as of C/EBPβ mediated enhanced VDR mediated 24(OH)ase transcription (FIG. 1, A–D). We found that in addition to kidney the regulation of C/EBPβ also contributes to the effects of $1,25(OH)_2D_3$ in osteoblastic cells (FIG. 1A, B). See Examples 2 and 3, herein. These findings establish C/EBPβ as a novel $1,25(OH)_2D_3$ target gene and indicate for the first time a role for C/EBPβ in the regulation of $1,25(OH)_2D_3$ induced 24(OH)ase transcription. These findings have led to the specific embodiments of the present invention.

Although specific embodiments of the present invention will now be described, it should be understood that such embodiments are by way of example only and merely illustrative of but a small number of the many possible specific embodiments that can represent applications of the principles of the present invention. Various changes and modifications obvious to one skilled in the art to which the present invention pertains are deemed to be within the spirit, scope and contemplation of the present invention as further defined in the appended claims.

The term "substantially identical" refers to nucleic acid or amino acid sequences having sequence variation that do not materially affect the nature of the protein (i.e. the structure, stability characteristics, substrate specificity and/or biological activity of the protein). With particular reference to nucleic acid sequences, the term "substantially identical" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially identical" refers generally to conservative substitutions and/or variations in regions of the polypeptide not involved in determination of structure or function. This includes the amino acids of the present invention in either their Dextrogyral or Levogyral optical isomer forms.

The present invention is directed to a novel pharmaceutical composition that includes a biologically acceptable carrier along with an effective amount of a C/EBPβ protein for the treatment and/or prevention of diseases associated with excess $1,25(OH)_2D_3$. The pharmaceutical composition includes a C/EBPβ protein encoded by an amino acid sequence substantially identical to the sequence of SEQ. ID. 2. The present invention is also directed to a pharmaceutical composition that includes an effective amount of a nucleotide sequence coding for the C/EBPβ protein, wherein the nucleotide sequence is substantially identical to the sequence of SEQ. ID. 1. An example of such diseased state that may be treated by the compositions of the present invention is hypercalcemia.

A method for the treatment of a disease associated with excess $1,25(OH)_2D_3$ in a subject is also provided. This method involves administering to the subject a pharmaceutical composition that includes an effective amount of a C/EBPβ protein or a nucleotide sequence coding for the C/EBPβ protein.

Methods for the delivery of nucleotide sequences to cells are well known in the recombinant arts. Such methods include, but are not limited to microinjection, calcium phosphatase, lyposomes, and electroporation. Genetic material, such as the nucleotides of the present invention, may be delivered to cells, in vivo, using various different plasmid based delivery platforms, including but not limited to ADV, AADV, MMLV, letniviral, and overall, retroviral gene delivery systems. These systems typically include a plasmid vector including a promoter sequence (such as CMV early promoter) operably linked to the nucleotide coding the gene of interest, as well as a Poly-A tail (such as the BGH) and the construction of the appropriate elements in a vector system containing the nucleotides of the present invention will be within the skills of one versed in the recombinant arts.

In a further embodiment, the present invention involves a method for reducing the risk of hypercalcemia when administering $1,25(OH)_2D_3$ or its analogs for the treatment of vitamin D deficient disease, which method includes the administration of a composition comprising the C/EBPβ protein, or a nucleotide sequence coding for the C/EBPβ, along with the administration of $1,25(OH)_2D_3$ or its analogs.

An additional embodiment of the present invention involves a method for testing the activity of C/EBPβ for determining whether a possible compound exhibits inhibitory effects on $1,25(OH)_2D_3$ activity in a cell such as LLCKL Kidney Cells, COS monkey cells, UMR Osteoblastic or skin cells, which includes the steps of:

(a) delivering the test compound to a viable cell;

(b) determining the amount of C/EBPβ mRNA or C/EBPβ in the cell following the delivery of the test compound; and (c) comparing the concentration determined (of mRNA or the C/EBPβ) to a control, wherein an increase in the amount of C/EBPβ mRNA or C/EBPβ in the cell relative to the control indicates the compound has an inhibitory effect on the concentration of $1,25(OH)_2D_3$ in the cell, where a decrease in the amount C/EBPβ mRNA or C/EBPβ in the cell relative to the control indicates the compound does not have an inhibitory effect and may increase the effectiveness of $1,25(OH)_2D_3$.

A further aspect of the present invention involves a method for determining whether a candidate compound activates or inhibits C/EBPβ activity, which includes the steps of:

(a) inducing C/EBPβ activity in vivo in a cell such as LLCKL Kidney Cells, COS monkey cells, UMR Osteoblastic or skin cells;

(b) biopsying the cells in which the C/EBPβ was induced;

(c) dividing the biopsied cells into two groups;

(d) adding a tagged monohydroxyvitamin $D_3$ to a first group of cells and thereafter measuring the amount of tagged dihydroxyvitamin $D_3$;

(e) adding a tagged monohydroxyvitamin $D_3$ plus the candidate compound to a second group of cells and thereafter measuring the amount of tagged dihydroxyvitamin $D_3$, wherein a lesser amount of tagged dihydroxyvitamin $D_3$ in the second group tested indicates activation and a greater or same amount indicates inhibition of C/EBPβ activity.

The present invention also includes a pharmaceutical composition containing a biologically acceptable carrier and an effective amount of a protein that inhibits C/EBPβ activity. A method for the treatment of a disease associated with a vitamin $D_3$ deficiency, which involves administering to a subject a pharmaceutical composition that includes an effective amount of such a compound that inhibits C/EBPβ activity, is also within the scope of the present invention.

The present invention encompasses pharmaceutical compositions prepared for storage or administration that comprise a therapeutically effective amount of one or more compounds of the present invention in a pharmaceutically acceptable carrier. The therapeutically effective amount of a compound of the present invention will be in the range of about 1 mu.g/kg to about 50 mg/kg. The particular dosage will depend on the route of administration, the type of mammal being treated, and the physical characteristics of the specific mammal under consideration, as well as the characteristics of the specific compound: for example, potency, bioavailability, metabolic characteristics, etc. These factors and their relationship to determining this amount are well known to skilled practitioners in the medical arts. This amount and the mode of administration can be tailored to achieve optimal efficiency and will be contingent on myriad factors recognized by those skilled in the medical arts, including weight, diet, and concurrent medication. The therapeutically effective amount of the compounds of the present invention can range broadly depending upon the desired effects and the therapeutic indication.

Pharmaceutically acceptable carriers for therapeutic use are well known in the pharmaceutical art, and are described, for example, in Remington's Pharmaceutical Sciences (A. P. Gennaro, ed.; Mack, 1985). For example, sterile saline or phosphate-buffered saline at physiological pH may be used. Preservatives, stabilizers, dyes, and even flavoring agents may be provided in the pharmaceutical composition. For example, sodium benzoate, sorbic acid, and esters of p-hydroxybenzoic acid may be added as preservatives (Id at 1449). Antioxidants and suspending agents may also be used (Id).

The pharmaceutical compositions of the present invention may be formulated and used as tablets, capsules, or elixirs for oral administration; suppositories for rectal or vaginal administration; sterile solutions and suspensions for parenteral administration; creams, lotions, or gels for topical administration; aerosols or insufflations for intratracheobronchial administration; and the like. Preparations of such formulations are well known to those skilled in the pharmaceutical arts. The dosage and method of administration can be tailored to achieve optimal efficacy and will depend on factors that those skilled in the medical arts will recognize.

When administration is to be parenteral, such as intravenous on a daily basis, injectable pharmaceuticals may be prepared in conventional forms, either as liquid solutions or suspensions; solid forms suitable for solution or suspension in liquid prior to injection; or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxiliary substances, such as wetting agents, pH buffering agents, and the like. If desired, absorption enhancing preparations (e.g. liposomes) may be utilized.

For these purposes, within the scope of the present invention is a kit for the delivery of the therapeutic agents described herein. The kit includes a therapeutic composition of the invention in an aqueous form (i.e., a solublized protein or nucleic acid sequence suspended in a stable buffer such as EDTA), a container for providing a composition of the invention and either (i) a device for delivering the composition of the invention to cells of an organism (e.g., a retractable needle or pulse voltage device), wherein the device is capable of being combined with the container, or (ii) instructions explaining how to deliver the composition of the invention with the device. Thus the "container" can include instructions furnished to allow one of ordinary skill in the art to make compositions of the invention. The instructions will furnish steps to make the compounds used for formulating nucleic acid molecules. Additionally, the instructions will include methods for testing compositions of the invention that entail establishing if the nucleic acid molecules are damaged upon injection after electroporation. The kit may also include notification of an FDA approved use and instructions.

A method for making a kit of the invention is also provided. The method involves the steps of combining a container for providing a composition of the invention with a stable buffer (such as EDTA) and either (i) a device for delivering the composition of the invention to the cells of an organism (e.g., a retractable needle or pulse voltage device), wherein the device is capable of being combined with the container, or (ii) instructions explaining how to deliver the composition of the invention with the pulse voltage device.

The polynucleotides of the present invention include isolated polynucleotides encoding the C/EBPβ polypeptides and fragments, and polynucleotides closely related thereto. More specifically, a C/EBPβ polynucleotide of the invention includes a polynucleotide comprising the human nucleotide sequences contained in SEQ ID NO: 1. C/EBPβ polynucleotides further include a polynucleotide comprising a nucleotide sequence that has at least 70% identity over its entire length to a nucleotide sequence encoding the C/EBPβ polypeptide of SEQ ID NO:1. In this regard, polynucleotides with at least 70% are preferred, more preferably at least 80% identity, even more preferably at least 90% identity, yet more preferably at least 95% identity, 97% are highly preferred and those with at least 98–99% are most highly preferred, with at least 99% being the most preferred. Also included under C/EBPβ polynucleotides are a nucleotide sequence which has sufficient identity to a nucleotide sequence contained in SEQ ID NO: 1 to hybridize under conditions useable for amplification (i.e., moderate to stringent conditions, as well known in the art) or for use as a probe or marker. The invention also provides polynucleotides that are complementary to such C/EBPβ polynucleotides.

Also included in the present invention are polynucleotides encoding polypeptides which have at least 70% identity, preferably at least 80% identity, more preferably at least 90% identity, yet more preferably at least 95% identity, even more preferably at least 97–99% identity, to the amino acid sequence of SEQ ID NO:2 over the entire length of the recited amino acid sequences.

In one aspect, the present invention relates to human C/EBPβ polypeptides. The human C/EBPβ polypeptides include the polypeptide of SEQ ID NO:2, as well as polypeptides comprising the amino acid sequence of SEQ ID NO: 2; and polypeptides comprising the amino acid sequence which have at least 70% identity to that of SEQ ID NO:2, over its entire length. Preferably C/EBPβ polypeptide exhibit at least at least one biological activity of C/EBPβ. The present invention further provides for a polypeptide which comprises an amino acid sequence which has at least 80% identity, more preferably at least 90% identity, yet more preferably at least 95% identity, most preferably at least 97–99% identity, to that of SEQ ID NO:2 over the entire length of SEQ ID NO:2.

In another aspect of the present invention methods for the competitive and selective inhibition of the 24(OH)ase promoter sequence is provided. By using recombinant techniques well known to those skilled in the art, mutated forms of the C/EBP β gene/protein can be obtained that contain mutations in the coding region that allows C/EBP β to bind to the 24(OH)ase promoter sequence, e.g., using site directed mutagenesis targeted to positions −395 to −388 or −964 to −955 of the C/EBP β gene (i.e., SEQ. ID. No. 1). The mutated forms of the C/EBP β protein can be screened to determine potential competitive inhibitors of 24(OH)ase enhancement, such screening mechanisms are well known to those skilled in the art.

A potential expression system allowing for the screening of competitive inhibitors of C/EBP β enhancement, would be to ligate the 24(OH)ase promoter to the Chloramphenical Acetyl Transferase (CAT) reporter gene using an appropriate plasmid and to transfect that plasmid into a suitable cell (such as LLCKL Kidney Cells, COS monkey cells or UMR Osteoblastic cells). The ability of a given C/EBP β mutated protein to inhibit 24(OH)ase enhancement can then be tested by introducing the mutated protein into the cell (e.g., by microinjection or co-transfecting a vector coding for the C/EBP β along with or without an inducible promoter) and determining its effect via CAT activity. Those C/EBP β mutated proteins which reduce or inhibit 24(OH)ase enhancement (i.e., by binding to the gene but not affecting enhancement) can then be selected and used for the treatment of calcium deficient diseases. This expression system can also be slightly modified and used to screen for small molecules that have an inhibitory effect on C/EBP β enhancement, as well. Selective inhibition can be achieved using recombinant nucleotides which encode an antisense sequence targeted to the C/EBP β binding site of the 24(OH)ase promoter. These sites are located at positions −395 to −388 and −964 to −955, in the promoter region of the 24(OH)ase gene. For a description of the 24(OH)ase gene and reporter region see: Ohyama, Y, Ozono, K et al J. Biol. chem. 269 10545–10550,1994 (rat 24(OH)ase promoter), Zierold, C, Darwish, H M and DeLuca, H. F. Proc. Natl. Acad. Sci USA 91:900–902 (1994), Kerry, D. M., Dwivedi, P. P et al J. Biol Chem 271: 29715–29721 (1996) and for the Human 24(OH)ase promoter—Chen K. S. and DeLuca H. F. Biochim. Biophys. Acta 1263: 1–9 (1995) herein incorporated by reference. Methods for generating antisense sequences are well known in the recombinant arts and standard protocols can be used. See the examples below for further details.

Hence, in another embodiment, a pharmaceutical composition containing a mutated C/EBPβ protein is provided. As an example, the mutated C/EBPβ protein may contain a defective 24(OH)ase binding region, i.e., caused by a mutation(s) in the nucleotide sequence coding for the C/EBPβ protein between basepairs −395 to −388 and basepairs −964 to −955 of SEQ. ID. 1. These mutations can be generated by standard procedures well known to those skilled in the art, such as by causing a point mutation. (i.e., by U.V. light) or by gene rearrangement. The pharmaceutical composition includes an acceptable biological carrier, wherein an effective amount it is suitable for treatment of a disease associated with diminished calcium absorption, such as osteoporosis. A method for the treatment of a disease associated with diminished calcium absorption in a subject, comprising administering to the subject a pharmaceutical composition that comprises an effective amount of a mutated C/EBPβ protein, is also provided.

Although certain preferred embodiments of the present invention have been described, the spirit and scope of the invention is by no means restricted to what is described above. For example, within the general framework of: SEQ. ID. 1 and 2 there is a very large number of permutations and combinations possible, all of which are within the scope of the present invention. The examples should not, therefore, be construed as specifically limiting the invention and variations of the invention, now known or later developed, are considered to fall within the scope of the present invention as hereinafter claimed.

EXAMPLE 1

Genechip Array Analysis

Studies were done using Affymetrix Gene Chip Array (Peng et al. *abstract ASBMR meeting*, October 2001) to study 1,25(OH)$_2$D$_3$ action in the kidney. Poly (A+) RNA was prepared from kidneys of vitamin D deficient mice (−D) or −D mice injected with 1,25(OH)$_2$D$_3$. cDNA was synthesized from poly(A+)RNA using Superscript. cRNA prepared using T7RNA polymerase, was purified and biotin labeled. The labeled probe was then hybridized by the staff of the Center for Applied Genomics, DNA Microarray Care facility UMDNJ—New Jersey Medical School to the corrected mouse Gene Chip probe array from Affymetrix and analyzed by Gene Chip 3.0 software. Most array hybridization signals did not change significantly upon 1,25(OH)$_2$D$_3$ treatment. Our results using Gene Chip array confirmed that the gene expressed in highest concentration in the kidney in response to 1,25(OH)$_2$D$_3$ is 24(OH)ase (43 fold compared to the kidneys of vehicle treated mice). Other genes activated by a factor greater than 50% by 1,25(OH)$_2$D$_3$ include C/EBPβ, an important activator of transcription and FK506 binding protein which has been reported to be important in steroid receptor trafficking as well as in modulating the steroid response.

The induction by 1,25(OH)$_2$D$_3$ of C/EBPβ was verified by Northern analysis not only in kidney but also in osteoblastic cells (FIGS. 1A–C). Western blot analysis also indicated induction by 1,25(OH)$_2$D$_3$ of C/EBPβ protein in primary murine osteoblasts (FIG. 1E). In addition, we have noted enhanced transcriptional response of 24(OH)ase in the presence of C/EBPβ (FIG. 1D). Thus by using this technology we have identified a novel 1,25(OH)$_2$D$_3$ target gene, C/EBPβ, and have used this information to provide new insight into the mechanism of 1,25(OH)$_2$D$_3$ induced 24(OH)ase transcription via C/EBPβ induction and activation. These findings establish C/EBPβ as a novel 1,25(OH)$_2$D$_3$ target gene that plays a key role in 24(OH)ase transcription.

EXAMPLE 2

Time Course/Dose Response Analysis

In time course (0–24 h) and dose response (10$^{-9}$–10$^{-7}$ 1,25(OH)$_2$D$_3$) studies we examined the induction by 1,25 (OH)$_2$D$_3$ of C/EBPβ mRNA in UMR osteoblastic cells, as well as in C/EBPβ kidney cells by Northern blot analysis, using C/EBPβ cDNA (pMEX C/EBPβ expression vector (from Dr. Simon Williams, Texas Tech University School of Medicine). cDNA is removed using NcoI and HindIII. The 400 bp fragment is the N terminal, which is not conserved among the isoforms and therefore is specific for C/EBPβ and therefore used for the Northern blot analysis. The time course of induction of C/EBPβ is compared to the time course of induction of 24(OH)ase and VDR mRNAs [24 (OH)ase cDNA is from K. Okuda and the rat VDR cDNA is from J. W. Pike]. The first significant induction of 24(OH) ase and VDR mRNAs in UMR cells is at 9 h after 1,25(OH)$_2$ D$_3$ treatment, compared to 3 h for C/EBPβ mRNA, FIG. 2A. Induction of C/EBPβ protein is examined by Western blot using nuclear extracts (antibody from Santa Cruz).

Whether 1,25(OH)$_2$D$_3$ can induce other isoforms of C/EBPβ can be determined using a 1000 bp NcoI fragment for C/EBPα and a 200 bp Nco I fragment for C/EBPδ as isoform specific cDNA probes (pMEX C/EBPβ and pMEX C/EBPβ have been obtained from Simon Williams).

To determine whether the effect of 1,25(OH)$_2$D$_3$ is at the level of transcription, studies are done using the rat C/EBPβ promoter (nested deletion constructs of the C/EBPβ gene promoter ligated into PGL-2 luciferase were obtained from Drs. Centrella and McCarthy). Transfections are done in LLCPK1 cells and UMR cells treated with 1,25(OH)$_2$D$_3$ (10$^{-9}$–10$^{-7}$M). At least 3 separate experiments are done using each cell type. For all studies related to VDR mediated 24(OH)ase transcription, significance is determined by Student's test or analysis of variance. Identification of a VDRE by deletion analysis may be performed to determine if regulation by 1,25(OH)$_2$D$_3$ is transcriptional.

EXAMPLE 3

The Determination of the Specificity of C/EBPβ for the Enhancement of 24(OH)ase Transcription Activation by 1,25(OH)$_2$D$_3$ of 24(OH)ase transcription (using the rat 24(OH)ase promoter (−1367/+74 phCAT) in the presence of C/EBPβ (using 0–8 µg pMEX C/EBPβ expression vector) is examined in LLCPK1 renal, in COS cells transfected with hVDR and osteoblastic cells. Two C/EBPβ sites are present in the rat 24(OH)ase promoter [at −395/−388 (TTGGCAAG) and at −964/−955 (TTCCAG-CAAT)]. To determine the involvement of each site in the C/EBPβ observed enhancement, rat 24(OH)ase promoter deletion mutants (671/+74 phCAT contains both VDREs at −151/−137 and −259/245 but not the distal C/EBPβ site; −291/+74 contains both VDREs but neither C/EBPβ site) can be used. Loss of C/EBPβ enhancement using the mutant constructs indicates the involvement of C/EBPβ binding sites in the 24(OH)ase promoter. Then, gel shift studies are done using both sites and GST C/EBPβ (from Drs. Centrella and McCarthy) to verify C/EBPβ binding to the putative site(s). The specificity of C/EBPβ for the enhancement of 24(OH)ase transcription is determined using the OPN promoter construct (−777/+79) from Dr. David Denhardt).

EXAMPLE 4

The Role of C/EBPβ in the Cross Talk Between PTH and the PKA Signaling Pathway and 1,25(OH)$_2$D$_3$ Since C/EBPβ is induced by protein kinase A activation in different cell types including osteoblasts and CREB binding sites are present in the C/EBPβ promoter it is indeed possible that the cross-talk of the PKA signaling pathway and PTH with 1,25(OH)$_2$D$_3$ may converge on changes in C/EBPβ expression. These studies determine whether pretreatment of osteoblastic cells with PTH (10 nM for 4 h) followed by treatment with 1,25(OH)$_2$D$_3$ (10 nM for a further 6 h) will result in enhanced C/EBPβ mRNA levels over the levels observed with PTH alone or 1,25(OH)$_2$D$_3$ alone. (The expression of VDR and 24(OH)ase mRNAs under the same conditions is also be examined.)

1,25(OH)$_2$D$_3$+PTH or 8-bromo cAMP has been shown to result in a 2–5 fold enhancement of 24(OH)ase and VDR mRNA levels in osteoblastic cells, above the levels observed with 1,25(OH)$_2$D$_3$ alone. C/EBPβ protein levels are examined by Western blot analysis. Studies are done in UMR cells, in MC-3T3E1 cells as well as in primary osteoblasts. Blots are probed for C/EBPα and C/EBPβ to determine the specificity for the β isoform and β actin is used as a control. At least 3 separate experiments are done per cell line or using primary osteoblasts. Cells are pretreated with 1,25 (OH)$_2$D$_3$ followed by treatment with PTH and various time and dose relationships are examined.

cAMP or PTH induced enhancement of 24(OH)ase transcription is due at least in part to an upregulation of VDR.

Since two putative C/EBPβ sites have been reported in the hVDR promoter (at −1490 and at −920; 143) the determination of the effect of C/EBPβ on VDR promoter activity is important. We have isolated the hVDR promoter fragment −1500/+60 by PCR and ligated it into the PGL-2 luciferase vector and found in our studies that C/EBPβ enhances PKA mediated transcription of the VDR (FIG. 2).

These studies are repeated using the VDR promoter (2–4 μg) in the presence of C/EBPβ expression vector (0–8 μg), the catalytic sub-unit of PKA expression vector (1 μg, MTCEVα from G. S. McKnight), or treatment with PTH (10 nM) or 8-bromo cAMP (1 mM) or 1,25(OH)$_2$D$_3$ (10 nM). Transfection is done using JEG cells (which are highly responsive to PKA activation and express VDR) or osteoblastic cells and the specificity for C/EBPβ using C/EBPα and C/EBPβ expression vectors is determined.

Transcriptional regulation of VDR is not well characterized. The CRE sites (putative sites are at −570 and at −361; 143) are identified by site directed mutagenesis (using the Stratagene site directed mutagenesis kit) and gel shift analysis (purified CREB is available from Robert Rehfuss, Bristol Myers Squibb, Princeton, N.J.). In addition, whether one or both C/EBPβ sites (at −1490 and −920; 142) is/are needed for the enhancement of PKA mediated transcription of VDR is determined using deletion analysis [Nco I site is at −1021 of the hVDR promoter (one-C/EBPβ site would remain) and an Eco RV site is at −590 (both C/EBPβ sites would be deleted but both CRE sites would be retained)] as well as gel shift analysis using both sites and GST C/EBPβ. From this it can be established that C/EBPβ is not only a novel 1,25(OH)$_2$D$_3$ target gene involved in the regulation of 24(OH)ase, but also is a key factor that plays an important role in the cross talk between PTH and 1,25(OH)$_2$D$_3$ action.

I claim:

1. A pharmaceutical composition comprising a C/EBPβ protein, wherein the amino acid sequence coding for the C/EBPβ protein has at least 95% identity to that of SEQ ID NO:2.

2. The pharmaceutical composition according to claim 1, further comprising a biologically acceptable carrier, wherein the pharmaceutical composition contains an effective amount of said C/EBPβ protein for the treatment of a disease associated with excess 1,25 $(OH)_2D_3$.

3. The pharmaceutical composition according to claim 2, wherein the disease associated with excess 1,25 $(OH)_2D_3$ to be treated is hypercalcemia.

4. A kit, comprising; a container for providing a composition of claim 1, and either (i) a device for delivering said composition to cells of an organism, wherein said device is capable of being combined with said container, or (ii) instructions explaining how to deliver said composition with said device.

5. A method for making a kit of claim 4, comprising the steps of combining a container for providing a composition of claim 1 or 3 with a biologically acceptable carrier and either (i) a device for delivering said composition to the cells of an organism, wherein said device is capable of being combined with said container, or (ii) instructions explaining how to deliver said composition with said device.

* * * * *

SEQUENCE LISTING

```
<160> NUMBER OF SEQ ID NOS: 2

<210> SEQ ID NO 1
<211> LENGTH: 953
<212> TYPE: DNA
<213> ORGANISM: Homo sapiens

<400> SEQUENCE: 1
atgcaacgcc tggtggcctg ggacccagca tgtctccccc tgccgccgcc gccgctttaa        60
atccatggaa gtggccaact tctactacga ggcggactgc ttggctgctg ggcggcaagg       120
cggcccccgc ggcgcccccc gcggccagac ccgggccgcg ccccggcga gctgggcagc        180 atcggcgacc acgagcgcgc catcgacttc agcccgtacc ccgctgggcg cgccgcaggc       240
cccggcgccc gccacggcca cggacaccTt cgaggccgcc cgcgcccgcc ccgcgcccg        300 cctcctccgg gcagcaccac gacttcctct ctcttctccg acgactacgg gggcaagaac       360
tgcaagaagc cggccgagta cggctagcct ggggcgcctg ggggctgcca agggcgcgct       420
gcaccccggc tgcttcgcgc cacccaccgc ccccgccgcc gccgccgccc gccgagctca       480
aggcggagcc gggctcccgc ggactgcaag cggaaggagg aggccggggc gccgggcggc       540
ggcgcaggca gcgggcttcc cgtacgcgct gcgcgcttac ctcggctacc aggcggtgcc       600
gagcgagcgg gagcctctcc acgtcctcct cgtccagccc gcccggcacg ccgagccccg       660 gccaaggcc ccccgaccgc ctgctacgcg ggggccgggc cggcgccctc gcaggagcaa        720
ggccaagaag accgtggaca agcacagcga cgagtacaag atccggcgcg aacaacatcg       780
```

```
ccgtgcgcaa gagccgcgac aaggccaaga tgcgcaacct ggagacacaa ggtcctggag      840
ctcacggccg agaacgagcg gctgcagaag aaggtggagc tcgcgcgagc tcagcaccct      900
gcggaacttg ttcaagcagc tgcccgagcc cctgctcctc cggccactgc tag             953

<210> SEQ ID NO 2
<211> LENGTH: 207
<212> TYPE: PRT
<213> ORGANISM: Homo sapiens

<400> SEQUENCE: 2

Ala Pro Ala Pro Ala Pro Ala Ser Ser Gly Gln His His Asp Phe Leu
1               5                   10                  15

Ser Asp Leu Phe Ser Asp Asp Tyr Gly Gly Lys Asn Cys Lys Lys Pro
            20                  25                  30

Ala Glu Tyr Gly Tyr Val Ser Leu Gly Arg Leu Gly Ala Ala Lys Gly
        35                  40                  45

Ala His Pro Pro Pro Pro Pro Pro Pro Pro Ala Glu Leu Lys Ala
    50                  55                  60

Glu Pro Gly Phe Glu Pro Ala Asp Cys Lys Arg Lys Glu Glu Ala Gly
65                  70                  75                  80

Ala Pro Gly Gly Gly Ala Gly Met Ala Ala Gly Phe Pro Tyr Ala Leu
                85                  90                  95

Arg Ala Gly Ser Ser Gly Ser Leu Ser Thr Ser Ser Ser Ser Ser Pro
            100                 105                 110

Pro Gly Thr Pro Ser Pro Ala Asp Ala Lys Ala Pro Pro Thr Ala Cys
        115                 120                 125

Tyr Ala Gly Ala Gly Pro Ala Pro Ser Gln Val Lys Ser Lys Ala Lys
    130                 135                 140

Lys Thr Val Arg Arg Glu Arg Asn Asn Ile Ala Val Arg Lys Ser Arg
145                 150                 155                 160

Asp Lys Ala Lys Met Arg Asn Leu Glu Thr Gln His Lys Val Leu Glu
                165                 170                 175

Leu Thr Ala Glu Asn Glu Arg Leu Gln Lys Lys Val Glu Gln Leu Ser
            180                 185                 190

Arg Glu Leu Ser Pro Glu Pro Leu Leu Ala Ser Ser Gly His Cys
        195                 200                 205
```